United States Patent
Bartsch et al.

(12)

(10) Patent No.: US 6,335,186 B1
(45) Date of Patent: Jan. 1, 2002

(54) PROCESS FOR THE PREPARATION OF L-PHOSPHINOTHRICIN BY A COUPLED ENZYMATIC REACTION

(75) Inventors: Klaus Bartsch, Steinbach; Gerd Fülling, Frankfurt am Main; Arno Schulz, Eppstein/Taunus, all of (DE)

(73) Assignee: Hoechst Aktiengesellschaft, Frankfurt am Main (DE)

( * ) Notice: Subject to any disclaimer, the term of this patent is extended or adjusted under 35 U.S.C. 154(b) by 0 days.

(21) Appl. No.: 08/408,178

(22) Filed: Mar. 22, 1995

Related U.S. Application Data

(63) Continuation of application No. 08/273,615, filed on Jul. 12, 1994, now abandoned, which is a continuation of application No. 08/130,148, filed on Sep. 17, 1993, now abandoned, which is a continuation of application No. 07/765,308, filed on Sep. 25, 1991, now abandoned.

(30) Foreign Application Priority Data

Sep. 27, 1990 (DE) .......................................... 40 30 578

(51) Int. Cl.⁷ ................................................. C12P 13/00
(52) U.S. Cl. ....................... 435/128; 435/106; 435/132; 435/131
(58) Field of Search ................................. 435/106, 128, 435/132, 131, 241

(56) References Cited

U.S. PATENT DOCUMENTS 4,826,766 A * 5/1989 Rozzell ........................ 435/106
5,130,246 A    7/1992 Schulz ......................... 435/193

FOREIGN PATENT DOCUMENTS

EP    0 135 846 A3    4/1985
EP    0 249 188 A2    12/1987
WO    WO 87/01727    3/1987

OTHER PUBLICATIONS

Bartsch Et Al., "Stereospecific . . . Phosphinothricin–Specific Transaminase from *Escherichia coli*," *Appl. and Environ. Microbiol.*, vol. 56, No. 1, pp. 712, 1990.*

Schulz Et Al., "Stereospecific . . . Phosphinothricin Specific Transaminase from *Escherichia coli*," *Appl. and Environ. Microbiol.*, vol. 56, No. 1, pp 1–6, 1990.*

Imai Et Al., "Enzymatic or Fermentative Manufacture of L–2–Amino–4–Hydroxymethylphosphinyl) Butyric Acid", *Chemical Abstracts* CA 109(2): 188830S 1988.*

Imai Et Al., "Microbial Process for the Production of 1–2–Amino–4–(Hydroxymethyphosphinyl)–Butyric Acid," *Chemical Abstracts*, CA 108(15): 130083p, 1987.*

*Enzyme Nomenclature*, Academic Press, 1992 p. 251, 253.*

* cited by examiner

*Primary Examiner*—Irene Marx
(74) *Attorney, Agent, or Firm*—Finnegan, Henderson, Farabow, Garrett and Dunner, L.L.P.

(57) ABSTRACT

A coupled enzyme reaction of a transaminase with GOT activity and of a transaminase with L-phosphinothricin transaminase activity produces phosphinothricin in virtually quantitative yield and virtually without any contamination whatever by a natural amino acid when the amino donor glutamate is employed in catalytic amounts and the amino donor aspartate is employed in approximately equimolar amounts relative to 4-(hydroxymethylphosphinyl)-2-oxobutyric acid.

11 Claims, No Drawings

PROCESS FOR THE PREPARATION OF L-PHOSPHINOTHRICIN BY A COUPLED ENZYMATIC REACTION

This application is a continuation of application Ser. No. 08/273,615, filed Jul. 12, 1994, now abandoned, which is a continuation of application Ser. No. 08/130,148, filed Sep. 17, 1993, abandoned, which is a continuation of application Ser. No. 07/765,308, filed Sep. 25, 1991, abandoned.

The invention relates to the synthesis of L-2-amino-4-(hydroxymethylphosphinyl)butyric acid (L-phosphinothricin) from 4-(hydroxymethylphosphinyl)-2-oxobutyric acid (HMPB) by coupling of two enzymatic reactions.

The preparation of phosphinothricin in a coupled enzymatic synthesis has already been disclosed in EP 249 188. This describes the conversion of α-ketoglutarate into glutamate in the presence of the amino donor aspartate and of a glutamate/oxalacetate transaminase (GOT). This conversion is coupled to another transaminase reaction which converts 4-(hydroxymethylphosphinyl)-2-oxobutyric acid (HMPB) into L-phosphinothricin in the presence of the amino donor glutamate formed in the first reaction.

Now, for complete substrate conversion in coupled enzyme reactions, it is important that the equilibrium constants of the individual enzyme reactions differ from one another. However, the equilibrium constant of transamination reactions is about 1.0 so that in general only a 50% yield of the required product is possible (U.S. Pat. No. 4,826,766).

It is possible to displace the equilibrium of enzymatic reactions in favor of the products either by removing one reaction product from the equilibrium or by employing an excess of one starting substance. In general the amino donor glutamate is employed in high excess for the said transamination reaction for synthesizing L-phosphinothricin [A. Schulz et al. (1990) Appl. Environ Micobiol. 56, 1–6, No. 1]. However, this has the disadvantage that the non-proteinogenous amino acid L-phosphinothricin can be separated from the natural amino acids, such as, for example, glutamate, only with great elaboration, for example by two consecutive ion exchange chromatographies [A. Schulz et al. (1990) Appl. Environ. Micobiol. 56, 1–6 No. 1].

An alternative possibility in a coupled process involving a phosphinothricin-specific transaminase and a GOT is for the reaction to be driven by the GOT in the direction of phosphinothricin synthesis by recycling the glutamate consumed by the phosphinothricin transaminase, because the GOT reaction product, oxalacetate, is spontaneously decarboxylated to pyruvate in the presence of doubly charged metal ions and is thus removed from the reaction equilibrium. However, all GOTs hitherto described have a subsidiary activity which transaminates pyruvate to alanine in the presence of glutamate, so that $NH_4^+$ is continuously removed from the reaction, and the reaction to give L-phosphinothricin cannot go to completion when equimolar amounts of HMPB and amino donor (glutamate and/or aspartate) are used. In addition, the resulting L-phosphinothricin is contaminated with alanine.

It has now been found that phosphinothricin is produced, in virtually quantitative yield and virtually without any contamination whatever by a natural amino acid, in a coupled enzyme reaction with a transaminase with GOT activity and with a transaminase with L-phosphinothricin transaminase activity when the amino donor glutamate is employed in catalytic amounts and the amino donor aspartate is employed in approximately equimolar amounts relative to HMPB.

Hence the invention relates to:

A process for the preparation of L-2-amino-4-(hydroxymethylphosphinyl)butyric acid (L-phosphinothricin) of the formula (I)

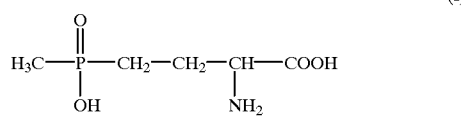

from 4-(hydroxymethylphosphinyl)-2-oxobutyric acid (HMPB) of the formula (II)

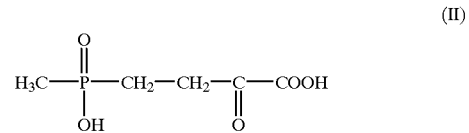

in a coupled enzyme reaction comprising the following steps:

a) reaction of aspartate and α-ketoglutarate in the presence of a suitable transaminase 1 to give oxalacetate and glutamate and b) reaction of glutamate and HMPB of the formula (II) in the presence of a suitable transaminase 2 to give α-ketoglutamate and L-phosphinothricin, wherein the molar ratio of aspartate to HMPB is 0.5–1.5 to 1, preferably 0.8–1.2 to 1, in particular equimolar, and glutamate or α-ketoglutarate is added in catalytic amounts.

Glutamate, aspartate and α-ketoglutarate or their corresponding acids are substances which can be be bought. HMPB can be prepared as described in EP 30424.

The transaminase 1 is any enzyme which has transaminase activity and is able to transaminate α-ketoglutarate to glutamate in the presence of aspartate as amino donor (so-called enzyme with GOT activity). It is preferable to use a GOT (glutamate/oxalacetate transaminase) which is unable to transaminate pyruvate to alanine and, in this way, would not contaminate the required product of the coupled reaction, L-phosphinothricin, with another natural amino acid. Pyruvate is produced, for example, by decarboxylation of oxalacetate, the transamination product of aspartate.

It is possible to use, in particular, transaminases which have GOT activity, from *Escherichia coli* (*E. coli*) or from bacteria of the genus Bacillus, and which have no pyruvate-specific activity.

The transaminase 2 is any enzyme which has transaminase activity and is able to transaminate HMPB to L-phosphinothricin in the presence of glutamate as amino donor. Enzymes of this type are indicated in EP 249 188. It is preferable to use as transaminase 2, in analogy to transaminase 1, a transaminase which is unable to transaminate pyruvate to alanine.

In particular, the L-phosphinothricin-specific transaminase from *E. coli* has no pyruvate-specific activity and can therefore be used by preference. The L-phosphinothricin-specific transaminase from *E. coli* can be concentrated, for example, by the method of A. Schulz (1990).

It is possible in principle also to use for the transamination reactions whole cells with the particular transaminase activity, cell extracts, partially purified cell extracts or purified enzymes. However, it is advantageous to employ enzymes which have been purified until subsidiary reactions no longer occur, especially the transamination of pyruvate to alanine.

It is particularly advantageous to employ at least one enzyme, in particular both, in immobilized form. A possible process for the immobilization of transaminases is described, for example, by A. Schulz et al. (1990).

The transamination reactions are generally carried out in a biocompatible buffer, i.e. in a buffer which maintains the pH in a range from 6.5 to 10, preferably 7.5 to 9.0, in particular 7.5 to 8.5, and does not react with the individual reactants. It is preferable to select a phosphate or tris buffer, in particular a tris buffer. The molar ratio of aspartate to HMPB is 0.5–1.5 to 1, preferably 0.8–1.2 to 1, in particular equimolar. Glutamate or α-ketoglutarate is added to the reaction mixture in catalytic amounts. The ratio of glutamate or α-ketoglutarate to HMPB is generally 0.01–1 to 1, preferably 0.01–0.2 to 1, in particular 0.05–0.2 to 1. The reaction mixtures generally also contain small amounts of the cofactor pyridoxal phosphate, for example in a concentration 1–500 μm, preferably 5–100 μm. The reaction temperature is generally between about 20 and 70° C., preferably from 30 to 400° C.

To increase the yield of L-phosphinothricin it is preferable to decarboxylate in the presence of multiply charged metal ions the oxalacetate produced in the glutamate/oxalacetate transaminase reaction (UK Patent Application 2 161 159). Examples of suitable multiply charged metal ions are all the metal ions listed in the British Patent Application, preferably $Al^{3+}$, $Mg^{2+}$, $Mn^{2+}$, $Fe^{2+}$ or $Fe^{3+}$. It is furthermore advantageous in this preferred embodiment to use no transaminase or transaminase fraction with an additional pyruvate-specific activity. The increase in the yield of L-phosphinothricin by the decarboxylation reaction of oxalacetate under the stated reaction conditions was completely unexpected because, according to UK Patent Application 2 161 159, the highest product yield was found only with aspartate as sole amino donor in the reaction system.

The virtually complete consumption of the amino donors aspartate and glutamate results in the product L-phosphinothricin being virtually free of natural amino acids, and separation of it from the formed α-keto acids α-ketoglutarate and oxalacetate or pyruvate is possible in a single step. Although α-ketoglutarate or glutamate has been added not in excess but only in very small amounts and, likewise, aspartate has been added not in excess but preferably equimolar relative to HMPB, nevertheless virtually complete conversion of HMPB into L-phosphinothricin has been observed. This was in no way predictable.

L-phosphinothricin can be purified straightforwardly by known processes, for example by extraction with methyl isobutyl ketone or by cation exchange chromatography, such as, for example, with Amberlite IR 120.

The L-phosphinothricin which is obtained is generally employed in agriculture as herbicide. The following examples are intended to explain the invention in more detail without restricting it in any way.

EXAMPLE 1

Synthesis of L-phosphinothricin By Biotransformation with *Escherichia coli* K-12

*E. coli* K-12 was cultivated in LB medium (10 g/l tryptone, 5 g/l yeast extract, 10 g/l NaCl) at 37° C. for 15 h. The bacterial cells were harvested by centrifugation at 5000 g for 10 min, washed twice in phosphate buffer (10 mM Na phosphate, pH=7.0, 10 mM NaCl) and then resuspended at a concentration of 100 mg/ml in the following solutions:
Solution 1
 HMPB: glutamic acid: aspartic acid=1:1:1
 100 mM HMPB
 100 mM glutamic acid
 100 mM aspartic acid
 50 mM tris/HCl, pH=8.0.
Solution 2
 HMPB: glutamic acid=1:4
 100 mM HMPB
 400 mM glutamic acid
 50 mM tris/HCl, pH=8.0.

The cell suspensions were incubated with the reaction mixtures at 37° C. The L-phosphinothricin content in the reaction mixtures was determined with an amino-acid analyzer at various times during the course of the synthesis. Table 1 shows the percent conversion into L-phosphinothricin during the course of the reaction for both biotransformation mixtures. Whereas the L-PPT yield did not exceed 85% with a four-fold excess of the amino donor glutamic acid (Solution 2), it was possible to achieve conversion rates of almost 100% with equimolar use of the amino donors glutamic acid and aspartic acid (Solution 1).

TABLE 1

L-phosphinothricin production with cells of *E. coli* K-12
L-phosphinothricin (% conversion)
Reaction mixtures

| Time (h) | L-phosphinothricin:Glu:Asp. = 1:1:1 | PPT:Glu = 1:4 |
|---|---|---|
| 2 | 1 | 2 |
| 4 | 3 | 4 |
| 24 | 23 | 36 |
| 48 | 71 | 72 |
| 120 | 94 | 78 |
| 165 | 96 | 82 |
| 218 | 98 | 86 |

EXAMPLE 2

Purification of Glutamate/Oxalacetate Transaminase from Pigs

EXAMPLE 3

Synthesis of L-phosphinothricin with Purified L-phosphinothricin-specific Transaminase from *E. coli* and GOT from Pigs at Various Glutamic Acid Concentrations The L-phosphinothricin-specific transaminase (PST) from *E. coli* K-12 (see EP-A 0 344 683) and the GOT from pig hearts (see Example 2) were dissolved at a concentration of 1 mg/ml in phosphate buffer (20 mM Na phosphate, pH=7.0, 0.1 mM pyridoxal phosphate, 1 mM 2-ketoglutarate, 5 mM β-mercaptoethanol). Then the volumes in each case corresponding to an activity of 1 unit (=1 μmol of L-phosphinothricin/min in the case of PST and 1 μmol of glutamate/min in the case of GOT) of the two enzymes were mixed and incubated with the following reaction solutions at 37° C. for 1 h:
 All reaction mixtures contained
 100 mM HMPB
 100 mM aspartic acid
 50 mM tris/HCl, pH=8.0
and additionally
 glutamic acid
 in Experiment 1:100 mM
 in Experiment 2:50 mM in Experiment 3:20 mM
in Experiment 4:10 mM
in Experiment 5:5 mM
in Experiment 6: -

The L-phosphinothricin content in the various mixtures after the reaction time was determined with an amino-acid analyzer (Biotronic LC 5001). The L-phosphinothricin synthesis rates calculated therefrom as percent conversion are compiled in Table 2. The experiments show that it is possible, with a negligible adverse effect on the rate of L-phosphinothricin synthesis, to reduce the glutamic acid concentration to 0.2 times that of the HMPB or aspartate employed.

TABLE 2

L-phosphinothricin synthesis at various glutamate concentrations

| Experiment | Reaction mixture | L-PPT (% conversion/h) |
|---|---|---|
| 1 | HMPB:Glu:Asp=1:1:1 | 55.5 |
| 2 | HMPB:Glu:Asp=1:0.5:1 | 48.5 |
| 3 | HMPB:Glu:Asp=1:0.2:1 | 43.5 |
| 4 | HMPB:Glu:Asp=1:0.1:1 | 30.6 |
| 5 | HMPB:Glu:Asp=1:0.05:1 | 18.9 |
| 6 | HMPB:Asp=1:1 | 3.0 |

EXAMPLE 4

Synthesis of L-phosphinothricin with Purified PST (*E. coli*) and GOT (Pig) at Various Enzyme Ratios The two purified transaminases were incubated as described in Example 3 with a reaction solution composed of 100 mM HMPB, 20 mM glutamic acid, 100 mM aspartic acid and 50 mM tris/HCl, pH=8.0 at 37° C. Various ratios of the activities of the two enzymes were employed for this:

1. 1 unit of PST/10 units of GOT
2. 1 unit of PST/1 unit of GOT
3. 1 unit of PST/0 unit of GOT The L-phosphinothricin content in the mixtures was determined at various times during the course of the synthesis reaction, measuring test samples in the amino-acid analyzer. The L-phosphinothricin syntheses calculated therefrom are shown in Table 3. The highest conversion was achieved with the enzyme ratio PST:GOT=1:1 (Mixture 2). The maximum PPT conversion rate achievable without addition of GOT (Mixture 3) was only about 20% because, in this case, only the glutamic acid but not the aspartic acid can be used for the synthesis of L-phosphinothricin.

TABLE 3

L-PPT synthesis with various enzyme ratios

| | % Conversion | | |
|---|---|---|---|
| Time (h) | PST:GOT = 1:10 (Mixture 1) | PST:GOT = 1:1 (Mixture 2) | PST:GOT:1:0 (Mixture 3) |
| 1 | 29 | 31 | 16 |
| 2 | 35 | 39 | 18 |
| 4 | 44 | 50 | 18 |
| 8 | 49 | 65 | 19 |
| 24 | 67 | 78 | 20 |
| 55 | 74 | 86 | 20 |

EXAMPLE 5

Effect of Manganese Chloride on L-phosphinothricin Synthesis

The purified transaminases were mixed in the ratio 1:1 (1 unit of each) as described in Example 3 and incubated with reaction solution (100 mM HMPB, 20 mM glutamic acid, 100 mM aspartic acid, 50 mM tris/HCl, pH=8.0) in the presence of 1 mM $MnCl_2$ without $MnCl_2$ at 37° C. The course of L-phosphinothricin synthesis was measured as described in Example 4 and is summarized in Table 4. It was possible distinctly to increase the reaction rate by adding manganese chloride. The L-phosphinothricin conversion after a reaction time of 24 h was about 10% higher than that in the comparison mixture without manganese chloride.

TABLE 4

Effect of manganese chloride on the L-PPT synthesis reaction

| | % Conversion | |
|---|---|---|
| Time (h) | +1 mM $MnCl_2$ | $-MnCl_2$ |
| 1 | 30 | 26 |
| 2 | 41 | 35 |
| 4 | 53 | 45 |
| 8 | 64 | 58 |
| 24 | 88 | 76 |

EXAMPLE 6

Immobilization of the "PST" Transaminase on Silica Gel 50 ml of activated silica gel (silanization and glutaraldehyde activation as described in the literature: K. Mosbach, Methods in Enzymology, Vol. XLIV; Academic Press, New York, 1976, pages 139 and 140) are added to 50 ml of PST solution (purified PST from *E. coli*, 10 mg of protein/ml of solution in 0.25 M potassium phosphate buffer, pH 8) and reaction is allowed to occur stirring gently for 3 h. The still moist catalyst is then filtered off and washed with 100 ml of 0.25 M phosphate buffer, pH 8. The biocatalyst prepared in this way can be employed for the reactions described below.

EXAMPLE 7

Immobilization of "GOT" Transaminase on Silica Gel 10 ml of a GOT solution (purified GOT from pigs, 8.4 mg of protein/10 ml of solution) are immobilized on 10 ml of silica gel as described in Example 6. The biocatalyst can be employed in this form for the coupled transamination.

EXAMPLE 8

Coupled Transamination with Immobilized PST and Immobilized GOT 180 mg (1 mmol) of HMPB, 133 mg (1 mmol) of L-aspartic acid, 29.4 mg (0.2 mmol) of L-glutamic acid, 10 mg of pyridoxal phosphate and 0.6 g of TRIS are made up with distilled water to 5 g of solution and adjusted to pH 8. To this are added 0.5 ml of immobilized PST (Example 6) and 0.5 ml of immobilized GOT (Example 7) and reaction is allowed to occur at pH 8 stirring cautiously at 26° C. for 48 h. The reaction mixture is investigated by HPLC (amino-acid analyzer) for the amino-acid content.

Yield (HPLC):
0.122 g of L-PPT (68% based on HMPB)
0.012 g of L-aspartic acid
0.028 g of L-glutamic acid
0.025 g of L-alanine

EXAMPLE 9

Coupled Transamination with Immobilized PST and Immobilized GOT 1 g (5.6 mmol) of HMPB, 715 mg (5.6 mmol) of L-aspartic acid, 163 mg (1.1 mmol) of L-glutamic acid and 10 mg of pyridoxal phosphate are made up with distilled water to 20 g of solution and adjusted to pH 8 with $KHCO_3$. After addition of 1 ml of immobilized PST (Example 6) and 1 ml of GOT (Example 7), reaction is allowed to take place stirring gently at 36° C. for 72 h. The product solution is investivated by HPLC (AAA) for the amino-acid content.

Yield (HPLC):

0.58 g of L-PPT (58% based on HMPB)

0.30 g of L-aspartic acid 0.16 g of L-glutamic acid 0.02 g of L-alanine

EXAMPLE 10

Coupled Transamination with Immobilized PST and Free GOT 180 mg (1 mmol) of HMPB, 147 mg (1 mmol) of L-glutamic acid, 133 mg (1 mmol) of L-aspartic acid, 10 mg of pyridoxal phosphate and 0.7 g of TRIS are made up with distilled water to 50 g of solution, pH 8, and 0.5 ml of immobilized PST from the solution from Example 6 and 42 µl of free GOT from the GOT solution prepared in Example 7 are added. The reaction is carried out stirring cautiously at 36° C. The amino-acid content in the solution after 48 h is investigated by HPLC (AAA).

Yield (HPLC):

0.145 g of L-PPT (80% based on HMPB)

0.024 g of L-aspartic acid 0.147 g of L-glutamic acid 0.003 g of L-alanine

EXAMPLE 11

Coupled Transamination with Immobilized PST and Immobilized GOT

The reaction is carried out in analogy to Example 10. 0.5 ml of immobilized GOT (Example 6) is employed in place of free GOT. The amino-acid composition in the product solution corresponds to that from Example 10.

The L-PPT content was determined by thin-layer chromatography. It is about 80%.

What is claimed is:

1. A process for the preparation of L-2-amino-4-(hydroxymethylphosphinyl)butyric acid of the formula (I):

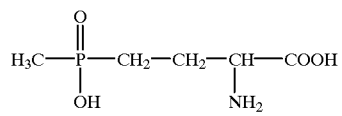

(I)

from 4-(hydroxymethylphosphinyl)-2-oxybutyric acid (HMPB) of the formula (II):

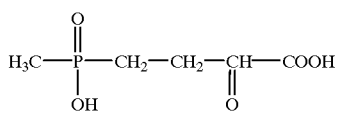

(II)

in a coupled enzyme reaction using isolated enzymes comprising the following steps:
 (a) reacting aspartate and α-ketoglutarate with an amount of transaminase 1 effective to give oxaloacetate and glutamate,
 (b) reacting the glutamate produced with HMPB of the formula (II) with an amount of a suitable transaminase 2 to produce α-ketoglutarate and L-2-amino-4-(hydroxymethylphosphinyl)butyric acid and
 (c) recovering said L-2-amino-4-(hydroxymethyl phosphinyl)butyric acid,
wherein the molar ratio of aspartate to HMPB is 0.8–1.2 to 1 and glutamate or α-ketoglutarate is added in catalytic amounts.

2. The process as claimed in claim 1, wherein glutamate or α-ketoglutarate is added in a molar ratio of 0.01–0.2 to 1 relative to HMPB.

3. The process as claimed in claim 1, wherein the transaminase 1 is a glutamate/oxalacetate transaminase.

4. The process as claimed in claim 3, wherein the glutamate/oxalacetate transaminase is obtained from *Escherichia coli* or Bacillus.

5. The process as claimed in claim 1, wherein the L-phosphinothricin-specific transaminase is obtained from *Escherichia coli*.

6. The process of claim 1, wherein oxaloacetate is decarboxylated to pyruvate in the presence of multiply charged cations.

7. The process of claim 6 wherein said multiply charged cations are selected from the group consisting of $Al^{3+}$, $Mg^{2+}$ $Mn^{2+}$, $Zn^{2+}$, $Fe^{2+}$, and $Fe^{3+}$.

8. The process of claim 1, wherein one or more of the transaminases are present in immobilized form.

9. The process as claimed in claim 8, wherein the immobilized transaminase or transaminases are present in a columnar reactor.

10. The process as claimed in claim 1 wherein the molar ratio of aspartate to HMPB is equimolar.

11. The process as claimed in claim 1, wherein glutamate or α-ketoglutarate is added in a molar ratio of 0.05–0.2 to 1 relative to HMPB.

* * * * *

UNITED STATES PATENT AND TRADEMARK OFFICE
CERTIFICATE OF CORRECTION

PATENT NO.    : 6,335,186 B1
DATED         : January 1, 2002
INVENTOR(S)   : Klaus Bartsch et al.

It is certified that error appears in the above-identified patent and that said Letters Patent is hereby corrected as shown below:

Column 8,
Line 24, "an amount of a suitable transaminase" should read -- an effective amount of a L-phosphinothricin-specific transaminase --.
Line 34, "oxalacetate" should read -- oxaloacetate --.
Line 45, "$Mg^{2+}Mn^{2+}$," should read -- $Mg^{2+}$, $Mn^{2+}$, --.

Signed and Sealed this

Third Day of September, 2002

*Attest:*

*Attesting Officer*

JAMES E. ROGAN
*Director of the United States Patent and Trademark Office*